United States Patent

Mogensen et al.

[11] Patent Number: 6,147,098
[45] Date of Patent: Nov. 14, 2000

[54] SUBSTITUTED GUANIDINES AND DIAMINONITROETHENES, THEIR PREPARATION AND USE

[75] Inventors: John Patrick Mogensen, Vanlose; John Bondo Hansen, Jyderup; Tina Moller Tagmose, Ballerup, all of Denmark

[73] Assignee: Novo Nordisk A/S, Bagsvaerd, Denmark

[21] Appl. No.: 09/306,308

[22] Filed: May 6, 1999

Related U.S. Application Data

[60] Provisional application No. 60/085,885, May 18, 1998.

[30] Foreign Application Priority Data

May 11, 1998 [DK] Denmark .............................. 00634/98

[51] Int. Cl.$^7$ ............................. A61K 31/44; A61K 31/16
[52] U.S. Cl. ......................... 514/357; 514/609; 546/330; 546/332; 564/104
[58] Field of Search ............................. 564/104; 514/609, 514/357; 546/330, 332

[56] References Cited

U.S. PATENT DOCUMENTS

| | | | |
|---|---|---|---|
| 4,567,188 | 1/1986 | Niemers et al. | 514/332 |
| 5,087,640 | 2/1992 | Morita et al. | 514/609 |

FOREIGN PATENT DOCUMENTS

| | | |
|---|---|---|
| 0 310 545 A2 | 4/1989 | European Pat. Off. . |
| 0 354 533 A2 | 2/1990 | European Pat. Off. . |
| 0 354 553 | 2/1990 | European Pat. Off. . |
| 0 405 525 A2 | 1/1991 | European Pat. Off. . |
| 94/22807 | 10/1994 | WIPO . |

OTHER PUBLICATIONS

Yoshizumi et al., Chem. Abst. 126:74528, 1996.
Myamoto et al., Chem Abst. 123:321699, 1995.
Yoshiizumi et al., Chem Pharm. Bull., vol. 44, No. 11, pp. 2042–2050 (1996).
Belezertseva et al. Chem Abst. 127:262499 (1997).
Abstract of Japanese patent application 06028936.
Abstract of Japanese patent application 3–244901 (Jan. 31, 1994).

*Primary Examiner*—Peter O'Sullivan
*Attorney, Agent, or Firm*—Steve T. Zelson; Carol E. Rozek

[57] ABSTRACT

Guanidine and diaminonitroethene derivatives represented by the formula

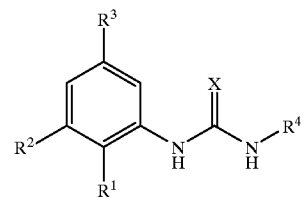

wherein X, $R^1$, $R^2$, $R^3$ and $R^4$ are defined in the description, compositions thereof and methods for preparing the compounds are described. The se compounds are useful in the treatment of diseases of the central nervous system, cardiovascular system, pulmonary system, gastrointestinal system and endocrinologic system.

40 Claims, No Drawings

SUBSTITUTED GUANIDINES AND DIAMINONITROETHENES, THEIR PREPARATION AND USE

CROSS-REFERENCE TO RELATED APPLICATIONS

This application claims priority under 35 U.S.C. 119 of U.S. provisional application Ser. No. 60/085,885 filed May 18, 1998 and Danish application no. PA 1998 00634 filed May 11, 1998, the contents of which are fully incorporated herein by reference.

FIELD OF THE INVENTION

The present invention relates to substituted guanidines and diaminonitroethenes, to methods for their preparation, to compositions comprising the compounds, to the use of these compounds as medicaments and their use in therapy, e.g. in the treatment of diseases of the central nervous system, the cardiovascular system, the pulmonary system, the gastrointestinal system and the endocrinologic system.

BACKGROUND OF THE INVENTION

Potassium channels play an important role in the physiological and pharmacological control of cellular membrane potential. Amongst the different types of potassium channels are the ATP-sensitive ($K_{ATP}$-) channels which are regulated by changes in the intracellular concentration of adenosine triphosphate. The $K_{ATP}$-channels have been found in cells from various tissues such as cardiac cells, pancreatic cells, skeletal muscles, smooth muscles, central neurons and adenohypophysis cells. The channels have been associated with diverse cellular functions for example hormone secretion (insulin from pancreatic beta-cells, growth hormone and prolactin from adenohypophysis cells), vasodilation (in smooth muscle cells), cardiac action potential duration, neurotransmitter release in the central nervous system.

Modulators of the $K_{ATP}$-channels have been found to be of importance for the treatment of various diseases. Certain sulphonylureas which have been used for the treatment of non-insulin-dependent diabetes mellitus act by stimulating insulin release through an inhibition of the $K_{ATP}$-channels on pancreatic beta-cells.

The potassium channel openers, which comprise a heterogeneous group of compounds, have been found to be able to relax vascular smooth muscles and have therefore been used for the treatment of hypertension.

In addition, potassium channel openers can be used as bronchodilators in the treatment of asthma and various other diseases.

Furthermore, potassium channel openers have been shown to promote hair growth, and have been used for the treatment of baldness.

Potassium channel openers are also able to relax urinary bladder smooth muscle and therefore, can be used for the treatment of urinary incontinence. Potassium channel openers which relax smooth muscle of the uterus can be used for treatment of premature labor.

By acting on potassium channels of the central nervous system these compounds can be used for treatment of various neurological and psychiatric diseases such as Alzheimer, epilepsy and cerebral ischemia.

Further, the compounds are found to be useful in the treatment of benign prostatic hyperplasia, erectile dysfunction and in contraception.

Compounds of the present invention, which inhibit insulin secretion by activating potassium channels of the beta-cell can be used in combination with other compounds which may be used to treat non-insulin dependent diabetes mellitus and insulin dependent diabetes mellitus. Examples of such compounds are insulin, insulin sensitizers, such as thiazolidinediones, insulin secretagogues, such as repaglinide, tolbutamide, glibenclamide and glucagon like peptide (GLP1), inhibitors of α-glucosidases and hepatic enzymes responsible for the biosynthesis of glucose.

Recently, it has been shown that diazoxide (7-chloro-3-methyl-2H-1,2,4-benzothiadiazine 1,1-dioxide) and certain 3-(alkylamino)-4H-pyrido[4,3-e]-1,2,4-thiadiazine 1,1-dioxide derivatives inhibit insulin release by an activation of KATP-channels on pancreatic beta-cells (Pirotte B. et al. *Biochem. Pharmacol*, 47, 1381–1386 (1994); Pirotte B. et al., *J. Med. Chem.*, 36, 3211–3213 (1993). Diazoxide has furthermore been shown to delay the onset of diabetes in BB-rats (Vlahos W D et al. *Metabolism* 40, 39–46 (1991)). In obese zucker rats diazoxide has been shown to decrease insulin secretion and increase insulin receptor binding and consequently improve glucose tolerance and decrease weight gain (Alemzadeh R. et al. Endocrinol. 133, 705–712, 1993). It is expected that compounds which activate $K_{ATP}$-channels can be used for treatment of diseases characterized by an overproduction of insulin and for the treatment and prevention of diabetes.

In EP 310545 and EP 306451, N-N'-substituted cyanoguanidines are claimed for the use as curing agent for epoxy resins.

In WO 9211233, U.S. Pat. No. 5,525,742-A, EP-747374-A1,EP 354553 and EP 405525 derivatives of the N-cyano-N'-aryl-N"-alkyl-guanidine type have been claimed as potassium channel activators related to smooth muscles.

Cyanoguanidines have recently been described by K. Yoshizumi et al Chem. Pharm. Bull. 44 (11) 2042–2050 (1996) and K. Yoshizumi et al Chem. Pharm. Bull. 45 (12) 2005–2010 (1997).

Derivatives of N-cyano-N'-aryl-N"-aryl-guanidines have been claimed in WO 9422807. N-aryl-N'-alkyl-2-nitro-1,1-ethenediamines have been described in U.S. Pat. No. 4,567,188. In J.Med.Chem 35 , 2327–2340 (1992) the synthesis of N-aryl-N'-alkyl-2-nitro-1,1-ethenediamine and N-heteroaryl-N'-alkyl-2-nitro-1,1-ethenediamine and their properties as agents for relaxation of smooth muscle are described.

Fluorine-containing arylcyanoguanidines have been described by E. G. Belezertseva et al in Khim.-Farm. Zh. (1997), 31 (6), 11–13.

DESCRIPTION OF THE INVENTION

The present invention relates to compounds of formula I:

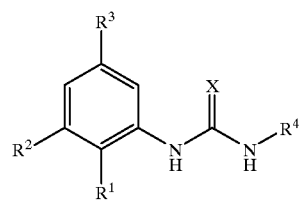

I wherein $R^1$ and $R^2$ are independently hydrogen, trifluoromethyl or halogen;

$R^3$ is trifluoromethyl, methoxy or halogen;

$R^4$ is straight or branched $C_{1-12}$-alkyl, $C_{2-12}$-alkenyl, $C_{2-12}$-alkynyl or $C_{3-8}$-cycloalkyl optionally substituted with $C_{3-8}$-cycloalkyl, halogen, hydroxy, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl, heteroarylalkyl or aryl, any or heteroaryl group optionally being substituted with halogen or trifluoromethyl; or $R^4$ is Y—$R^5$, Y being —O—or —N($R^6$)—;

$R^5$ and $R^6$ are independently straight or branched $C_{1-12}$-alkyl, $C_{2-12}$-alkenyl, $C_{2-12}$-alkynyl or $C_{3-8}$-cycloalkyl optionally substituted with $C_{3-8}$-cycloalkyl, halogen, hydroxy, heteroaryl, heteroarylalkyl, aryloxy or aryl, any aryl or heteroaryl group optionally being substituted with halogen or trifluoromethyl;

or $R^5$ and $R^6$ together with the nitrogen atom form a 3–12 membered mono- or bicyclic system, in which one or more of the carbon atoms may be exchanged with nitrogen, oxygen or sulfur, each of these ring systems optionally being mono- or polysubstituted with halogen, $C_{1-6}$-alkyl, hydroxy, $C_{1-6}$-alkoxy, $C_{1-6}$-alkoxy-$C_{1-6}$-alkyl, nitro, amino, cyano, trifluoromethyl, $C_{1-6}$-monoalkyl- or dialkylamino or oxo;

X is N—CN or CH—$NO_2$;

or a salt thereof with a pharmaceutically acceptable acid or base, or any optical isomer or mixture of optical isomers, including a racemic mixture, or any tautomeric form thereof.

The salts include pharmaceutically acceptable acid addition salts, pharmaceutically acceptable metal salts or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, tartaric, fumaric, mandelic, benzoic, cinnamic, methane-sulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkylthio" as used herein, alone or in combination, refers to a straight or ranched monovalent substituent comprising a lower alkyl group linked through a divalent sulfur atom having its free valence bond from the sulfur atom and having 1 to 6 carbon atoms e.g. methylthio, ethylthio, propylthio, butylthio, pentylthio.

The term "cycloalkyl" as used herein refers to a radical of a saturated cyclic hydrocarbon with the indicated number of carbons such as cyclopropyl, cyclobutyl, cyclopentyl, or cyclohexyl.

The terms "$C_{2-12}$-alkenyl" as used herein refers to an unsaturated hydrocarbon chain having 2–6 or 2–18 carbon atoms and one double bond such as e.g. vinyl, 1-propenyl, allyl, isopropenyl, n-butenyl, n-pentenyl and n-hexenyl.

The term "$C_{2-12}$-alkynyl" as used herein refers to unsaturated hydrocarbons which contain triple bonds, such as e.g. —C≡CH, —C≡CCH$_3$, —CH$_2$C≡CH, —CH$_2$CH$_2$C≡CH, —CH(CH$_3$)C≡CH, and the like.

The term "$C_{1-6}$-alkoxy-$C_{1-6}$-alkyl" as used herein refers to a group of 2–12 carbon atoms interrupted by an 0 such as e.g. CH$_2$—O—CH$_3$, CH$_2$—O—CH$_2$—CH$_3$, CH$_2$—O—CH(CH$_3$)$_2$ and the like.

The term "halogen" means fluorine, chlorine, bromine or iodine.

The term "perhalomethyl" means trifluoromethyl, trichloromethyl, tribromomethyl or triiodomethyl.

The terms "$C_{1-12}$-alkyl", as used herein, alone or in combination, refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl and the like. The term "$C_{1-18}$-alkyl" as used herein also includes secondary $C_{3-6}$-alkyl and tertiary $C_{4-6}$-alkyl.

The term "$C_{1-6}$-monoalkylamino" as used herein refers to an amino group wherein one of the hydrogen atoms is substituted with a straight or branched, saturated hydrocarbon chain having the indicated number of carbon atoms such as e.g. methylamino, ethylamino, propylamino, n-butylamino, sec-butylamino, isobutylamino, tert-butylamino, n-pentylamino, 2-methylbutylamino, n-hexylamino, 4-methylpentylamino, neopentylamino, n-hexylamino, 2,2-dimethylpropylamino and the like.

The term "$C_{1-6}$dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino, and the like.

The term "3–12 membered mono- or bicyclic system" as used herein refers to a monovalent substituent of formula —NR$^2$R$^3$ or —NR$^{11}$R$^{12}$ where R$^2$ and R$^3$, or R$^{11}$ and R$^{12}$ together with the nitrogen atom form a 3–12 membered mono- or bicyclic system, in which one or more of the carbon atoms may be exchanged with nitrogen, oxygen or sulfur, such as 1-pyrrolidyl, piperidino, morpholino, thiomorpholino, 4-methylpiperazin-1-yl, 7-azabicyclo[2.2.1]heptan-7-yl, tropanyl and the like.

The term "aryl" as used herein refers to phenyl, 1-naphthyl, or 2-naphthyl.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine, and purine.

The term "arylalkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "arylalkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroarylalkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio, and the like.

In a preferred embodiment of the invention $R^3$ is selected from trifluoromethyl and $R^2$ from hydrogen or trifluoromethyl.

In another preferred embodiment of the invention $R^2$ and $R^3$ are selected from halogen and $R^4$ is branched $C_{1-12}$-alkyl.

Further preferred compounds are those where $R^2$ and $R^3$ are selected from halogen and $R^4$ is $C_5$-alkyl, branched at the C(2), C(3) or C(4) carbon atom counted from the attachment to the nitrogen atom, in particular compounds where $R^2$ and $R^3$ both are chloro.

Preferred compounds of the invention are:

N-Cyano-N'-(3,5-bis(trifluoromethyl)phenyl)-N"-(3-methylbutyl)guanidine

N-Cyano-N'-(3,5-bis(trifluoromethyl)phenyl)-N"-(2-(4-pyridinyl)ethyl)guanidine

N-Cyano-N'-(3,5-bis(trifluoromethyl)phenyl)-N"-(1,2,2-trimethylpropyl)guanidine

N-Cyano-N'-(3,5-bis(trifluoromethyl)phenyl)-N"-(3-cyclopentylpropyl)guanidine

N-Cyano-N'-(3,5-bis(trifluoromethyl)phenyl)-N"-(2-cyclopropylethyl)guanidine

N-Cyano-N'-(3,5-bis(trifluoromethyl)phenyl)-N"-(cyclopentyl)guanidine

N-Cyano-N'-(3,5-bis(trifluoromethyl)phenyl)-N"-(1,2-dimethylpropyl)guanidine

N-Cyano-N'-(3,5-bis(trifluoromethyl)phenyl)-N"-(2-chlorobenzyl)guanidine

N-Cyano-N'-(3,5-bis(trifluoromethyl)phenyl)-N"-(3-chlorobenzyl)guanidine

N-Cyano-N'-(3,5-dichlorophenyl)-N"-(2-chlorobenzyl)guanidine

N-Cyano-N'-(3,5-dichlorophenyl)-N"-(3-cyclopentylpropyl)guanidine

N-Cyano-N'-(3,5-dichlorophenyl)-N"-(3-cyclopentyl)guanidine

N-Cyano-N'-(3,5-dichlorophenyl)-N"-(2-cyclopropylethyl)guanidine

N-(3,5-bis(trifluoromethyl)phenyl)-N'-(1,2,2-trimethylpropyl)-2-nitro-1,1-ethenediamine N-(3,5-bis(trifluoromethyl)phenyl)-N'-(3-methylbutyl)-2-nitro-1,1-ethenediamine N-(3,5-bis(trifluoromethyl)phenyl)-N'-(3-cyclopentylpropyl)-2-nitro-1,1-ethenediamine N-(3,5-bis(trifluoromethyl)phenyl)-N'-(2-cyclopropylethyl)-2-nitro-1,1-ethenediamine N-(3,5-bis(trifluoromethyl)phenyl)-N'-(cyclopentyl)-2-nitro-1,1-ethenediamine N-(3,5-bis(trifluoromethyl)phenyl)-N'-((1,2-dimethylpropyl)-2-nitro-1,1-ethenediamine N-(3,5-bis(trifluoromethyl)phenyl)-N'-(2-chlorobenzyl)-2-nitro-1,1-ethenediamine N-(3,5-bis(trifluoromethyl)phenyl)-N'-(3-chlorobenzyl)-2-nitro-1,1-ethenediamine N-(3,5-dichlorophenyl)-N'-(1,2,2-trimethylpropyl)-2-nitro-1,1-ethenediamine N-(3,5-dichlorophenyl)-N'-(3-cyclopentylpropyl)-2-nitro-1,1-ethenediamine N-(3,5-dichlorophenyl)-N'-(cyclopentyl)-2-nitro-1,1-ethenediamine N-(3,5-dichlorophenyl)-N'-(2-chlorobenzyl)-2-nitro-1,1-ethenediamine N-(3,5-dichlorophenyl)-N'-(3-chlorobenzyl)-2-nitro-1,1-ethenediamine N-(3,5-dichlorophenyl)-N'-(2-cyclopropylethyl)-2-nitro-1,1-ethenediamine N-Cyano-N'-[3,5-bis(trifluoromethyl)phenyl]-N"-(1,1-dimethylpropyl)guanidine N-Cyano-N'-(3,5-bis(trifluoromethyl)phenyl)-N"-(1-methylethyl)-guanidine N-Cyano-N'-[3,5-bis(trifluoromethyl)phenyl]-N"-propyl-guanidine N-Cyano-N'-(3-trifluoromethylphenyl)-N"-cyclopentylguanidine N-Cyano-N'-isopropyl-N"-(3-trifluoromethylphenyl)guanidine N-Cyano-N'-(3,5-dichlorophenyl)-N"-(2-chlorobenzyl)guanidine N-Cyano-N'-cyclopentyl-N"-(3,5-dichlorophenyl)guanidine N-Cyano-N'-(3,5-dichlorophenyl)-N"-(1-methylethyl)guanidine N-Cyano-N'-(3,5-dichlorophenyl)-N"-propylguanidine N-Cyano-N'-(3,5-dichlorophenyl)-N"-(3-methylbutyl)-guanidine N-Cyano-N'-cyclopentyl-N"-(3-methyloxy-5-trifluoromethylphenyl)guanidine and N-Cyano-N'-(3-methoxy-5-trifluoromethylphenyl)-N"-(3-methylbutyl)guanidine.

The use of the following known compounds as medicaments and their use in therapy, e.g. in the treatment of diseases in the endocrinologic system is also a preferred embodiment of the invention:

N-Cyano-N'-(3-trifluoromethylphenyl)-N"-(1,2,2-trimethylpropyl)guanidine

N-Cyano-N'-(3,5-dichlorophenyl)-N"-(1,2,2-trimethylpropyl)-guanidine

N-Cyano-N'-(3,5-dichlorophenyl)-N"-(1,1-dimethylpropyl)guanidine

N-Cyano-N'-(3,5-dichlorophenyl)-N"-(1,1-dimethylbutyl)guanidine

N-Cyano-N'-(3,5-dichlorophenyl)-N"-t-pentylguanidine

N-Cyano-N'-(3,5-dichlorophenyl)-N"-(1-ethyl-1-methylpropyl)guanidine

N-Cyano-N'-(3,5-dichlorophenyl)-N"-t-butylguanidine

N-Cyano-N'-(3,5-dichlorophenyl)-N"-(1,1,2-trimethylpropyl)guanidine and

N-Cyano-N'-(3,5-dichlorophenyl)-N"-(1,1-diethylpropyl)guanidine.

The compounds of the present invention interact with the potassium channels and hence act as openers or blockers of the ATP-regulated potassium channels, which make them useful in the treatment of various diseases of the cardiovascular system, e.g. cerebral ischemia, hypertension, ischemic heart diseases, angina pectoris and coronary heart diseases; the pulmonary system; the gastrointestinal system; the central nervous system and the endocrinologic system.

Since some $K_{ATP}$-openers are able to antagonize vasospasms in basilar or cerebral arteries the compounds of the present invention can be used for the treatment of vasospastic disorders such as subarachnoid hemorrhage and migraine.

The compounds of the present invention may also be used for the treatment of diseases associated with decreased skeletal muscle blood flow such as Raynauds disease and intermittent claudication.

Further, the compounds of the invention may be used for the treatment of chronic airway diseases, including asthma, and for treatment of detrusor muscle instability secondary to bladder outflow obstruction and therefore for kidney stones by aiding their passage along the urethra.

The present compounds could also be used for treatment of conditions associated with disturbances in gastrointestinal mobility such as irritable bowel syndrome. Additionally these compounds can be used for the treatment of premature labor and dysmenorrhea.

Potassium channel openers hyperpolarize neurons and inhibit neurotransmitter release and it is expected that such compounds can be used for the treatment of various diseases of the central nervous system, e.g. epilepsia, ischemia and neurodegenerative diseases, and for the management of pain.

Further, potassium channel openers promote hair growth; therefore, the compounds of the present invention can be used for the treatment of baldness.

Potassium channel openers also relax urinary bladder smooth muscle; thus, the compounds of the present invention can be used for the treatment of urinary incontinence.

In diseases such as nesidioblastosis and insulinoma in which a hypersecretion of insulin causes severe hypoglycemia the compounds of the present invention can be used to reduce insulin secretion. In obesity hyperinsulinemia and insulin resistance is very frequently encountered. This condition could lead to the development of non-insulin dependent diabetes mellitus (NIDDM). It is expected that potassium channel openers, and hence the compounds of the present invention, can be used for reducing the hyperinsulinemia and thereby prevent diabetes and reduce obesity. In overt NIDDM treatment of hyperinsulinemia with potassium channel openers, and hence the present compounds, can be of benefit in restoring glucose sensitivity and normal insulin secretions.

Owing to the efficiency of the present compounds to improve glucose sensitivity they are useful for the treatment and/or prevention of ailments and disorders involving elevated plasma blood glucose, such as hyperglycemia. Furthermore, they may find use in the treatment and/or prevention of dyslipidemia, Type I diabetes, NIDDM, hypertriglyceridemia, syndrome X, insulin resistance, impaired glucose tolerance, obesity, diabetic dyslipidemia, hyperlipidemia and hypertension.

In early cases of insulin dependent diabetes (IDDM) or in prediabetic cases, potassium channel openers and hence the present compounds can be used to induce pancreatic cell rest which may prevent the progression of the autoimmune disease.

The potassium channel openers of the present invention can be administered in combination with an immunosuppressant or with an agent like nicotinamide, which will reduce autoimmune degeneration of beta-cells.

Combining beta-cell rest with a treatment protecting the beta-cells against cytokine mediated beta-cell impairment/cytotoxicity is another aspect of this invention. Insulin requiring or Type 1 diabetes (IDDM) as well as late onset IDDM (also known as type 1.5. e.g. non-insulin-requiring Type 2 (NIDDM) patients with autoreactivity against beta-cell epitopes that later turns insulin requiring) have circulating autoreactive monocytes/lymphocytes that homes to the islets/beta-cells and releases their cytokines. Some of these cytokines (e.g. interleukin-1b (IL-1b), tumor necrosis factor α (TNFα) and interferon γ (IFNγ)) are specifically toxic to the beta-cells, e.g. through the induction of nitric oxide (NO) and other free radicals. Inhibition of this cytotoxicity, e.g. by co-administering nicotinamide (NA), a derivative hereof or other cytokine protective compounds to the prediabetic/diabetic patients treated with the PCO compound is an example of this aspect. Nicotinamide belongs to the B-vitamin family and is derived from nicotinic acid by amidation of the carboxyl group. It processes none of nicotine's pharmacological properties. NA is converted into NAD+, which acts as a coenzyme for proteins involved in tissue respiration. NA has been proposed to influence several of the putative intracellular molecular events following immune attack on the beta-cells. Animal experiments and early non-blinded experiments in humans have indicated a protective role of this compound against IDDM as well as in cytokine/immune mediated beta-cell destruction.

Yet another aspect of this application concerns the use of a PCO compound alone or in combination with the inhibitor of cytokine/immune mediated beta-cell impairment, in transplantation, e.g. islet transplantation into diabetes patients. The use of one or both of these treatments may reduce the risk of rejection of the transplanted islets/beta-cells/engineered beta-cells/pancreas.

Compounds of the present invention which act as blockers of KATP-channels can be used for the treatment of NIDDM.

Preferably, the compounds of the present invention may be used for treatment or prevention of diseases of the endocrinologic system such as hyperinsulinemia and diabetes.

Accordingly, in another aspect the invention relates to a compound of formula I or a pharmaceutically acceptable acid addition salt thereof for use as a therapeutically acceptable substance, preferably for use as a therapeutically acceptable substance in the treatment of hyperinsulinemia and treatment or prevention of diabetes.

Furthermore, the invention also relates to the use of the inventive compounds of formula I as medicaments useful for treating hyperinsulinemia and treating or preventing diabetes.

Optionally, the pharmaceutical composition of the invention may comprise a compound of formula I combined with one or more other pharmacologically active compounds, e.g. an antidiabetic or other pharmacologically active material, including compounds for the treatment and/or prophylaxis of insulin resistance and diseases wherein insulin resistance is the pathophysiological mechanism. Suitable antidiabetics comprise insulin as well as orally active hypoglycaemic agents such as sulphonylureas, e.g. glibenclamide and glipizide; biguanides, e.g. metformin; benzoic acid derivatives, e.g. repaglinide; and thiazolidinediones, e.g. troglitazone and ciglitazone.

The compounds of the present invention may be prepared by various methods known to those skilled in the art. For example the methods for preparation of 2-nitro-1,1-ethenediamines by Niemers et al. U.S. Pat. No. 4,567,188 and P. W. Manley et al. J.Med.Chem. 35, 2327–2340 (1992):

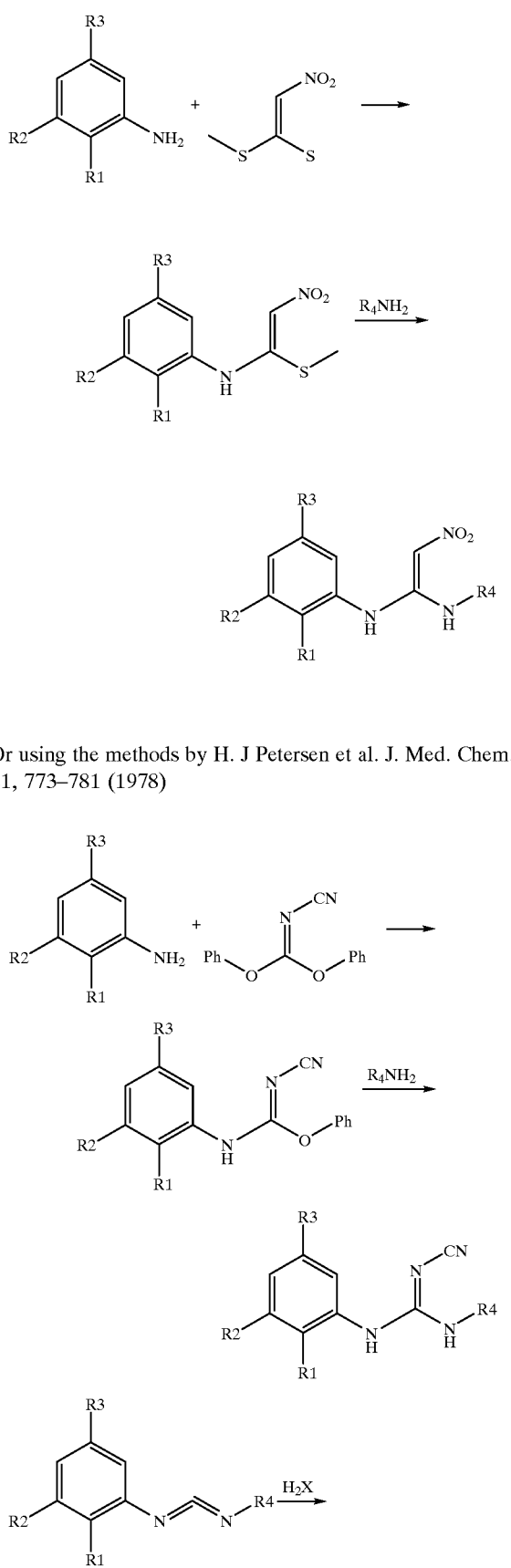

Or using the methods by H. J Petersen et al. J. Med. Chem. 21, 773–781 (1978)

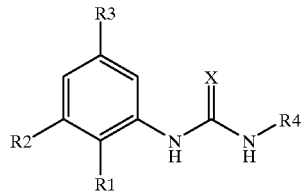

X = NCN, CHNO$_2$

The starting materials are either known compounds or compounds which may be prepared in analogy with the preparation of known compounds or in analogy with known methods as described in Kogyo Kagaku Zashi, 59, (6) 1–33 (1956) and Zh. Obshch. Khim., 35, 2055 (1965).

Pharmacological Methods

The ability of the compounds to interact with potassium channels can be determined by various methods. When patch-clamp techniques (Hamill O. P., Marty A., Neher E., Sakmann B. and Sigworth F. J., Plügers Arch., 391, 85–100 (1981)) are used the ionic current through a single channel of a cell can be recorded.

The activity of the compounds as potassium channel openers can also be measured as relaxation of rat aorta rings according to the following procedure:

A section of rat thoracic aorta between the aortic arch and the diaphragm was dissected out and mounted as ring preparations as described by Taylor P. D. et al, Brit J. Pharmacol, 111, 42–48 (1994).

After a 45 min. equilibration period under a tension of 2 g, the preparations were contracted to achieve 80% of the maximum response using the required concentration of phenylephrine. When the phenylephrine response reached a plateau, potential vasodilatory agents were added cumulatively to the bath in small volumes using half log molar increments at 2 min intervals. Relaxation was expressed at the percentage of the contracted tension. The potency of a compound was expressed as the concentration required to evoke a 50% relaxation of the tissue.

Relaxation of rat aorta rings

Example 1 EC$_{50}$ 5.6 micro M

In the pancreatic b-cell the opening of the K$_{ATP}$-channels can be determined by measuring the subsequent change in the concentration of cytoplasmic free Ca$^{2+}$ concentration according to the method of Arkhammar P. et al., J. Biol. Chem., 262, 5448–5454 (1987).

An opening of K$_{ATP}$-channels will result in an efflux of potassium ions. By measuring the release of $^{86}$Rb$^+$ (a radioactive potassium mimic) from e.g. beta-cells pre-incubated in the presence of $^{86}$Rb$^+$ the effect of compounds acting as potassium channel openers can be determined. The test expresses the ability of the compounds to regulate the secretion of insulin from the beta-cells.

$^{86}$Rb$^+$ efflux from a β-cell line

The RIN 5F cell line was grown in RPMI 1640 with Glutamax I, supplemented with 10% fetal calf serum (from GibcoBRL, Scotland, UK) and maintained in an atmosphere of 5% CO$_2$/95% air at 37° C. The cells were detached with a Trypsin-EDTA solution (from GibcoBRL, Scotland, UK), resuspended in medium, added 1 mCi/ml $^{86}$Rb$^+$ and replated into microtiter plates (96 well cluster 3596, sterile, from Costar Corporation, Mass., USA) at a density of 50000 cells/well in 100 μl/well, and grown 24 hours before use in assay.

The plates were washed 4 times with Ringer buffer (150 mM NaCl, 10 mM Hepes, 3.0 mM KCl, 1.0 mM $CaCl_2$, 20 mM Sucrose, pH 7.1). Eighty $\mu l$ Ringer buffer and 1 $\mu l$ control- or test compound dissolved in DMSO was added. After incubation 1 h at room temperature with a lid, 50 $\mu l$ of the supernatant was transferred to PicoPlates (Packard Instrument Company, CT, USA) and 100 $\mu l$ MicroScint40 (Packard Instrument Company, CT, USA) added. The plates were counted in TopCount (Packard Instrument Company, CT, USA) for 1 min/well at the 32p program.

The calculation of $EC_{50}$ and $E_{max}$ was done by SlideWrite (Advanced Graphics Software, Inc., CA, USA) using a four parameter logistic curve: $y=(a-d)/(1+(x/c)b)+d$, where a=the activity estimated at concentration zero, b=a slope factor, c=the concentration at the middle of the curve and, d=the activity estimated at infinite concentration. $EC_{50}$=c and $E_{max}$=d, when the curve is turned of at infinite concentrations.

Increased Rb-efflux in rin 5F cells

Example 1 $EC_{50}$ 2.6 micro M

The effect of $K_{ATP}$-channel modulators on pancreatic beta-cells can be determined by measuring qualitative changes in membrane potential in the insulin producing cell line β-TC3 using fluorescence imaging techniques.

The slow fluorescent membrane potential probe DiBAC was used. The cells were kept in $Ca^{2+}$-HEPES buffer supplemented with 10 mM glucose. After 5 s of each 60 s run the compound was added. 48 wells were run in each set, taking about 1 h. The same cells were then run again, now adding 25 mM KCl after 5 s, and the depolarisation-induced increase in DiBAC fluorescence monitored for 55 s.

In addition the effect of $K_{ATP}$-channel modulators on pancreatic beta-cells can be determined by measuring the increase or decrease in insulin release from insulin producing beta-cell lines or isolated islets.

Effect of $K_{ATP}$-channel modulators can be measured using the following procedure:

The beta cells are cultured with change of media every three-four days. Cells are then seeded in 96 well microtiter dishes and cultured for three day at 38° C., 5% $CO_2$ and 95% humidity.

The cells are washed with NN-buffer (+10 mM Hepes+ 0.1% BSA) for one minute and glucose (final conc. 22 mM), IBMX (final conc.0.1 mM) and compounds (final conc. from $5\times10^{-5}$ M–$5\times10^{-8}$ M) added. All cells are then incubated for three hours (38° C., 5% $CO_2$ and 95% humidity).

Supernates are harvested into Greiner minisorb microtiter wells and frozen. Insulin is measured using elisa-techniques.

The compounds according to the invention are effective over a wide dose range. In general satisfactory results are obtained with dosages from about 0.05 to about 1000 mg, preferably from about 0.1 to about 500 mg, per day. A most preferable dosage is about 1 mg to about 100 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph.Eur. |
| Avicel ® | 31.4 mg |
| Amberlite ® | 1.0 mg |
| Magnesii stearas | 0.25 mg Ph.Eur. |

EXAMPLES

The process of preparing the compounds of formula I is further illustrated in the following examples which, however, are not to be construed as limiting.

Example 1

N-Cyano-N'-(3,5-bis(trifluoromethyl)phenyl)-N"-(3-methylbutyl)guanidine a) N-(3,5-bis(trifluoromethyl)phenyl)-N'-cyano-O-phenylisourea A solution of diphenylcyanocarbonimidate (2 mmol, 476 mg), 3,5 bistrifluoromethylaniline (2 mmol, 458 mg) and triethylamine (2 mmol, 202 mg) in dichloromethane (15 ml) was stirred under nitrogen for 12 h. After concentration the residue was stirred with toluene (5 ml) for 2 h and the solid was collected by filtration giving 550 mg of N-(3,5-bis (trifluoromethyl)phenyl)-N'-cyano-O-phenylisourea (73.6%);

$^1$H-NMR (d$_6$-DMSO): δ7.25 (m, 5H), 7.95 (s,1H), 8.15 (s, 2H), 11.2 (s,1H).

b) N-Cyano-N'-(3,5-bis(trifluoromethyl)phenyl)-N"-(3-methylbutyl)guanidine

A solution of N-(3,5-bis(trifluoromethyl)phenyl)-N'-cyano-O-phenylisourea (1 mmol, 373 mg), 3-methylbutylamine (1.15 mmol,100 mg) and triethylamine (1.5 mmol, 150 mg) in acetonitrile (2 ml) was stirred for 24 h at 60° C. After concentration the residue was purified by column chromatography (heptane:ethyl acetate 1:1) to give the title compound (100 mg, 27%).

$^1$H-NMR (d$_6$-DMSO): δ 0.9 (d, 6H),1.45 (q, 2H), 1.65 (m,1H), 3.3 (q,2H), 7.7 (t, 1H), 7.79 (s, 1H), 7.95 (s, 2H), 9.45 (s,1H).

Example 2

N-Cyano-N'-(3,5-bis(trifluoromethyl)phenyl)-N"-(2-(4-pyridinyl)ethyl)guanidine

By following a procedure analogous to the one described in EXAMPLE 1b, N-(3,5-bis(trifluoromethyl)-phenyl)-N'-cyano-O-phenylisourea (1 mmol, 373 mg) was treated with 4-(2-aminoethyl)pyridine (1.15 mmol, 140.5 mg) to give 110 mg (27%) of the title product;

$^1$H-NMR (d$_6$-DMSO): δ 3.0 (t, 2H), 3.75 (q,2H), 7.41 (d,2H), 7.89 (s,1H), 7.95 (s, 1H), 8.05 (s, 2H), 8.62 (d, 2H), 9.5 (s,1H).

Example 3

N-Cyano-N'-(3,5-bis(trifluoromethyl)phenyl)-N"-(cyclopentyl)guanidine

To a suspension of N-(3,5-bis(trifluoromethyl)phenyl)-N'-cyano-O-phenylisourea (0.400 g, 1.1 mmol) in dry acetonitrile (2.5 ml) triethylamine (0.164 ml, 1.2 mmol) and cyclopentylamine (0.116 ml, 1.2 mmol) was added. The homogenous solution was stirred at 85° C. under N$_2$ for 3.5 h. The solvent was evaporated, and the residue was dissolved in ethyl acetate and washed with water twice. The organic layer was dried (Na$_2$SO$_4$) and concentrated. The crude product was purified by flash chromatography using ethyl acetate/heptane 1:2 to give the title compound. Yield 82% (0.320 g). mp 156–159° C.

$^1$H-NMR(CDCl$_3$): δ 8.87 (1H, broad s, NH); 7.78 (2H, s); 7.60 (1H, s); 5.50 (1H, broad d, NH); 4.20 (1H, sextet); 2.1 (2H, m); 1.75 (4H m); 1.55 ppm (2H, m).

Example 4

N-Cyano-N'-(3,5-bis(trifluoromethyl)phenyl)-N"-(2-chlorobenzyl)guanidine

By following a procedure analogous to the one described above in Example 1b, N-(3,5-bis(trifluoromethyl)phenyl)-N'-cyano-O-phenylisourea (0.300 g, 0.8 mmol) was treated with triethylamine (0.123 ml, 0.88 mmol) and 2-chlorobenzylamine (0.107 ml, 0.88 mmol) to give the title compound as a syrup. Yield 72% (0.234 g).

$^1$H-NMR(CDCl$_3$): δ 8.6 (1H, broad s, NH); 7.70 (3H, s); 7.45 (2H, m); 7.30 (2H,m); 5.85 (1H, broad s, NH); 4.60 (2H, d).

Example 5

N-Cyano-N'-[3,5-bis(trifluoromethyl)phenyl]-N"-(1,2-dimethylpropyl)guanidine a) N-[3,5-bis(trifluoromethyl)phenyl]-N'-cyano-O-phenylisourea A solution of diphenylcyanocarbonimidate (2 mmol, 476 mg), 3,5-bis(trifluoromethyl)aniline (2 mmol, 458 mg) and triethylamine (2 mmol, 202 mg) in dichloromethane (15 ml) was stirred under nitrogen for 12 h. After concentration the residue was stirred with toluene (5 ml) for 2 h and the solid was collected by filtration giving 550 mg of N-[3,5-bis (trifluoromethyl)phenyl]-N'-cyano-O-phenylisourea (73.6%);

$^1$H-NMR (d$_6$-DMSO): δ 7.25 (m, 5H), 7.95 (s, 1H), 8.15 (s, 2H), 11.2 (s, 1H).

b) N-Cyano-N'-[3,5-bis(trifluoromethyl)phenyl]-N"-(1,2-dimethylpropyl)guanidine

A solution of N-[3,5-bis(trifluoromethyl)phenyl]-N'-cyano-O-phenylisourea (0.8 mmol, 300 mg), 3-methyl-2-butylamine (0.88 mmol, 0.101 ml) and triethylamine (0.88 mmol, 0.123 ml) in acetonitrile (2 ml) was stirred for 7 h at 75° C. After concentration the residue was dissolved in ethyl acetate, washed with water, dried (Na$_2$SO$_4$) and concentrated. The residue was purified by column chromatography (heptane:ethyl acetate 4:1) to give the title compound (143 mg, 59%) as white crystals. Mp 134–136° C.; EI SP/MS: 366 (M+); $^1$H-NMR (CDCl$_3$): δ 0.92 (d, 6H),1.15 (d, 3H), 1.78 (m, 1H), 3.78 (m, 1H), 4.85 (br, 1H), 7.73 (br s, 3H), 8.0 ppm (br, 1H); MA calc for C$_{15}$H$_{16}$F$_6$N$_4$:C, 49.18%; H, 4.40%; N, 15.29%. Found: C, 48.95%; H, 4.38%; N 15.08%.

Example 6

N-Cyano-N'-[3,5-bis(trifluoromethyl)phenyl]-N"-(1,2,2-trimethylpropyl)guanidine

A solution of N-[3,5-bis(trifluoromethyl)phenyl]-N'-cyano-O-phenylisourea (0.8 mmol, 300 mg), 2-amino-3,3-dimethylbutane (0.88 mmol, 0.09 g) and triethylamine (0.88 mmol, 0.123 ml) in acetonitrile (2 ml) was stirred for 8 h at 75° C. After concentration the residue was purified by column chromatography (heptane:ethyl acetate 2:1) to give the title compound (140 mg, 46%) as white crystals. Mp 165.5–166.5° C.; EI SP/MS: 380 (M+); $^1$H-NMR (CDCl$_3$): δ 0.92 (s, 9H),1.13 (d, 3H), 3.8 (m, 1H), 4.8 (br d, 1H), 7.74 (br s, 3H), 8.5 ppm (br, 1H); MA calc for C$_{16}$H$_{18}$F$_6$N$_4$: C, 50.53%; H, 4.77%; N, 14.73%. Found: C, 50.48%; H, 4.74%; N, 14.45%.

Example 7

N-Cyano-N'-[3,5-bis(trifluoromethyl)phenyl]-N"-(1,1-dimethylpropyl)guanidine

A solution of N-[3,5-bis(trifluoromethyl)phenyl]-N'-cyano-O-phenylisourea (0.78 mmol, 290 mg), tert-amylamine (0.85 mmol, 0.100 ml) and triethylamine (0.85 mmol, 0.119 ml) in acetonitrile (2 ml) was stirred for 25 h at 75° C. followed by work-up as described in EXAMPLE 5, b) to give the title compound (140 mg, 46%) as white crystals. Mp 149–150° C.; EI SP/MS: 366 (M+); $^1$H-NMR (CDCl$_3$): δ 0.85 (t, 3H),1.35 (s, 6H), 1.75 (q, 2H), 4.65 (br s,1H), 7.70 (br s, 3H), 8.95 ppm (br s, 1H); MA calc for C$_{15}$H$_{16}$F$_6$N$_4$. 0.15 H$_2$O: C, 49.37%; H, 4.57%; N, 14.76%. Found: C, 49.72%; H, 4.56%; N, 14.76%.

Example 8

N-Cyano-N'-(3,5-bis(trifluoromethyl)phenyl)-N"-(1-methylethyl)-guanidine

N-[3,5-bis(trifluoromethyl)phenyl]-N'-cyano-O-phenylisourea (0.94 mmol, 350 mg) and isopropylamine (1 ml) was stirred in a sealed flask for 19 h at 75° C. After concentration the residue was dissolved in dichloromethane, washed with 1 N aqueous HCl (2×), water, dried (Na$_2$SO$_4$) and concentrated. The residue was crystallized from ethyl acetate and heptane to give the title compound (114 mg, 45%) as white crystals. Mp 176–182° C.; $^1$H-NMR (CDCl$_3$): δ 1.25 (d, 6H), 4.07 (m, 1H), 5.5 (br d, 1H), 7.71 (br s, 1H), 7.75 (br s, 2H), 8.10 ppm (br, 1H); MA calc for C$_{13}$H$_{12}$F$_6$N$_4$:

C, 46.16%; H, 3.58%; N, 16.56%. Found: C, 46.15%; H, 3.64%; N, 16.45%.

Example 9
N-Cyano-N'-[3,5-bis(trifluoromethyl)phenyl]-N"-propyl-guanidine

N-[3,5-bis(trifluoromethyl)phenyl]-N'-cyano-O-phenylisourea (0.94 mmol, 350 mg) and n-propylamine (1 ml) was stirred in a sealed flask for 19 h at 75° C. After concentration the residue was dissolved in dichloromethane, washed with 1 N aqueous HCl (2×), water, dried ($Na_2SO_4$) and concentrated. The residue was purified by flash chromatography (ethyl acetate/heptane 1:2) to give the title compound (90 mg, 28%) as white crystals. Mp 142.5–143.5° C.; $^1$H-NMR ($CDCl_3$): δ 0.95 (t, 3H), 1.65 (sextet, 2H), 3.35 (q, 2H), 5.45 (br, 1H), 7.68 (br s, 1H), 7.80 (br s, 2H), 8.35 ppm (br, 1H); MA calc for $C_{13}H_{12}F_6N_4$: C, 46.16%; H, 3.58%; N, 16.56%. Found: C, 46.31%; H, 3.65%; N, 16.23%.

Example 10
N-Cyano-N'-(3-trifluoromethylphenyl)-N"-cyclopentylguanidine a) N-(3-trifluoromethylphenyl)-N'-cyano-O-phenylisourea To a solution of 3-trifluoromethylaniline (11 mmol, 1.37 ml) in dichloromethane (25 ml), diphenylcyanocarbonimidate (10 mmol, 2.38 g), and triethylamine (11 mmol, 1.53 ml) were added. The mixture was stirred under nitrogen for 23 h. After concentration the residue was stirred with water, the water was decanted followed by concentration. The residue was stirred with toluene and the solid was collected by filtration giving 1.42 g of N-(3-trifluoromethylphenyl)-N'-cyano-O-phenylisourea (50%);

$^1$H-NMR ($CDCl_3$): δ 7.13 (d, 2H), 7.30 (t, 1H), 7,42 (t, 2H), 7.43 (d, 2H), 7.60 (m, 1H), 7.68 (s, 1H), 9.3 ppm (brs, 1H). EI SP/MS: 305 (M+).

b) N-Cyano-N'-(3-trifluoromethylphenyl)-N"-cyclopentylguanidine

N-(3-Trifluoromethylphenyl)-N'-cyano-O-phenylisourea (1 mmol, 290 mg) was stirred for 19 h at 80° C. in cyclopentylamine (1 ml). After concentration of the cold reaction mixture, the residue was dissolved in dichloromethane, washed with 1 N aqueous HCl (2×), water, dried ($Na_2SO_4$) and concentrated. The residue was purified by column chromatography (heptane:ethyl acetate 3:1) to give the title compound (205 mg, 68%) as a syrup. Crystallisation from heptane:ethyl acetate 2:1 gave 147 mg (49%). Mp 111.5–113° C; $^1$H-NMR ($CDCl_3$): δ 1.42 (m, 2H), 1.65 (m, 4H), 2.05 (m, 2H), 4.12 (sextet, 1H), 4.85 (br, 1H), 7.35 (br s,1H), 7.5 ppm (m, 4H); MA calc for $C_{14}H_{15}F_3N_4$: C, 56.75%; H, 5.10%; N, 18.91%. Found: C, 56.48%; H, 5.08%; N, 18.65%.

Example 11
N-Cyano-N'-isopropyl-N"-(3-trifluoromethylphenyl)guanidine

To a solution of N-(3-trifluoromethylphenyl)-N'-cyano-O-phenylisourea (0.98 mmol, 286 mg) in dry acetonitrile (2 ml), isopropylamine (0.184 ml) and triethylamine (0.150 ml) were added. The mixture was stirred for 42 h at room temperature under nitrogen. After concentration the residue was purified by flash chromatography (ethyl acetate/heptane 1:2) to give the title compound (210 mg, 79%) as a syrup. Crystallization from ethyl acetate / heptane 1:3 gave white crystals (165 mg, 62%). Mp 109–111° C.; $^1$H-NMR ($CDCl_3$): δ 1.20 (d, 6H), 4.05 (m,1H), 4.67 (br d, 1H), 7.42 (m, 1H), 7.50 (s,1H), 7.55 (m, 2H), 7.68 ppm (br, 1H); MA calc for $C_{12}H_{13}F_3N_4$: C, 53.33%; H, 4.85%; N, 20.73%. Found: C, 53.61%; H, 4.92%; N, 20.67%.

Example 12
N-Cyano-N'-(3,5-dichlorophenyl)-N"-(2-chlorobenzyl)guanidine a) N-Cyano-N'-(3,5-dichlorophenyl)-O-phenylisourea To a solution of 3,5-dichloroaniline (11 mmol, 1.79 g) in dichloromethane (25 ml), diphenylcyanocarbonimidate (10 mmol, 2.38 g) and triethylamine (11 mmol, 1.53 ml) were added. The reaction mixture was stirred under nitrogen for 65 h at room temperature. After concentration the residue was stirred with water, the water was decanted followed by concentration. The residue was stirred with toluene and the solid was collected by filtration giving 2.04 g of the title compound (67%); $^1$H-NMR ($CDCl_3$): δ 7.12 (d, 2H), 7.22 (s, 1H), 7,35 (m, 3H), 7.45 (d, 2H), 9.4 ppm (br s,1H). EI SP/MS: 305 (M+), 307 (M+2), 309 (M+4).

b) N-Cyano-N'-(3,5-dichlorophenyl)-N"-(2-chlorobenzyl)guanidine

To a solution of N-(3,5-dichlorophenyl)-N'-cyano-O-phenylisourea (0.8 mmol, 250 mg) in dry acetonitrile (2 ml), 2-chlorobenzylamine (0.9 mmol, 0.108 ml) and triethylamine (0.125 ml) were added. The mixture was stirred for 2½ h at 82° C. under nitrogen. After concentration the residue was recrystallized from ethyl acetate to give the title compound (208 mg, 72%). Mp 186–187.5° C.; $^1$H-NMR ($CDCl_3$): δ 4.54 (d, 2H), 5.53 (br, 1H), 7.15 (m, 2H), 7.3 (m, 3H), 7.4 (m, 2H), 7.75 ppm (br, 1H); EI SP/MS: 394 (M+). MA calc for $C_{15}H_{11}Cl_3N_4$: C, 50.95%; H, 3.14%; N, 15.84%. Found: C, 50.68%; H, 3.10%; N, 15.49%.

Example 13
N-Cyano-N'-cyclopentyl-N"-(3,5-dichlorophenyl)guanidine

To a solution of N-(3,5-dichlorophenyl)-N'-cyano-O-phenylisourea (0.8 mmol, 250 mg) in dry acetonitrile (2 ml), cyclopentylamine (0.9 mmol, 0.089 ml) and triethylamine (0.125 ml) were added. The mixture was stirred for 2½ h at 82° C. under nitrogen. After concentration the residue was purified by flash chromatography (ethyl acetate/heptane 1:2) to give the title compound (160 mg, 66%) as crystals. Mp 147.5–148.5° C.; $^1$H-NMR ($CDCl_3$): δ 1.45 (m, 2H), 1.65 (m, 4H), 2.05 (m, 2H), 4.11 (sextet, 1H), 5.1 (br, 1H), 7.2 (m, 3H), 8.02 ppm (br, 1H); EI SP/MS: 296 (M+), 298 (M+2), 300 (M+4). MA calc for $C_{13}H_{14}Cl_2N_4$: C, 52.54%; H, 4.75%; N, 18.85%. Found: C, 52.17%; H, 4.71%; N, 18.50%.

Example 14
N-Cyano-N'-(3,5-dichlorophenyl)-N"-(1-methylethyl)guanidine

N-(3,5-Dichlorophenyl)-N'-cyano-O-phenylisourea (0.98 mmol, 300 mg) and isopropylamine (1 ml) was stirred in a sealed flask for 19 h at 75° C. After concentration the residue was dissolved in dichloromethane, washed with 1 N aqueous HCl (2×), water, dried ($Na_2SO_4$) and concentrated. The residue was crystallized from ethyl acetate/heptane 1:3 to give the title compound (115 mg, 43%) as white crystals. Mp 156–158.5° C.; $^1$H-NMR ($CDCl_3$): δ 1.21 (d, 6H), 4.03 (m,1H), 4.70 (br d,1H), 7.16 (m, 2H), 7.29 (m,1H), 7.47 ppm (br,1H); MA calc for $C_{11}H_{12}Cl_2N_4$: C, 48.73%; H, 4.46%; N, 20.66%. Found: C, 48.76%; H, 4.49%; N, 20.38%.

Example 15
N-Cyano-N'-(3,5-dichlorophenyl)-N"-propylguanidine

N-(3,5-Dichlorophenyl)-N'-cyano-O-phenylisourea (0.98 mmol, 300 mg) and n-propylamine (1 ml) was stirred in a sealed flask for 19 h at 75° C. After concentration the residue was dissolved in dichloromethane, washed with 1 N aqueous HCl (2×), water, dried ($Na_2SO_4$) and concentrated. The residue was purified by flash chromatography (ethyl acetate/ heptane 1:3) to give the title compound (60 mg, 23%) as white crystals. Mp 141–143° C.; $^1$H-NMR (CDCl$_3$): δ 0.92 (d, 6H), 1.58 (sextet, 2H), 3.25 (q, 1H), 5.1 (br, 1H), 7.19 (m, 2H), 7.25 (m, 1H), 7.95 ppm (br, 1H); MA calc for C$_{11}$H$_{12}$Cl$_2$N$_4$: C, 48.73%; H, 4.46%; N, 20.66%. Found: C, 49.02%; H, 4.55%; N 20.27%.

Example 16

N-Cyano-N'-(3,5-dichlorophenyl)-N"-(3-methylbutyl)-guanidine

To N-(3,5-Dichlorophenyl)-N'-cyano-O-phenylisourea (0.98 mmol, 300 mg) in dry acetonitrile (2 ml), 3-methylbutylamine (2.16 mmol, 0.255 ml) and triethylamine (1.08 mmol, 0.150 ml) were added. The reaction mixture was stirred for 16 h at 85° C. under nitrogen. The precipitated material was filtered off and recrystallized from ethyl acetate to give the title compound (160 mg, 54%) as white crystals. Mp 146.5–1451.5° C.; $^1$H-NMR (CDCl$_3$): δ 0.94 (d, 6H), 1.43 (q, 2H), 1.6 (m, 1H), 3.31 (q, 2H), 4.9 (br, 1H), 7.18 (br s, 2H), 7.29 (br s, 1H), 7.5 ppm (br, 1H); MA calc for C$_{13}$H$_{16}$Cl$_2$N$_4$: C, 52.19%; H, 5.39%; N, 18.73%. Found: C, 52.23%; H, 5.51%; N, 18.60%.

Example 17

N-Cyano-N'-cyclopentyl-N"-(3-methyloxy-5-trifluoromethylphenyl)guanidine

N-Cyano-N'-(3-methoxy-5-trifluoromethyl-phenyl)-O-phenylisourea

To a solution of 3-methyloxy-5-trifluoromethylaniline (11 mmol, 2.10 g) in dichloromethane (25 ml), diphenylcyanocarbonimidate (10 mmol, 2.38 g) and triethylamine (11 mmol, 1.53 ml) were added. The reaction mixture was stirred under nitrogen for 16 h at room temperature. After concentration the residue was stirred with water, the water was decanted followed by concentration. The residue was purified by flash chromatography (ethyl acetate/heptane 1:2) to give 0.413 g of the title compound (12%); Mp 168.5–169.5° C.; $^1$H-NMR (CDCl$_3$): δ 3.83 (s, 3H), 7.00 (s, 1H), 7.14 (m, 3H), 7,23 (s, 1H), 7.32 (t, 1H), 7.43 ppm (t, 2H), 8.7 (br s, 1H). EI SP/MS: 335 (M+).

N-Cyano-N'-cyclopentyl-N"-(3-methyloxy-5-trifluoromethylphenyl)guanidine

To a solution of N-Cyano-N'-(3-methoxy-5-trifluoromethyl-phenyl)-O-phenylisourea (0.52 mmol, 175 mg) in dry acetonitrile (1 ml), cyclopentylamine (1.04 mmol, 0.113 ml) and triethylamine (0.080 ml) were added. The mixture was stirred for 19 h at 75° C. under nitrogen. After concentration the residue was dissolved in dichloromethane, washed with 1 N aqueous HCl (2×), water, dried (Na$_2$SO$_4$) and concentrated. The residue was purified by flash chromatography (ethyl acetate/heptane 1:2) to give a syrup. Crystallisation from ethyl acetate/heptane 1:4 gave grey crystals (110 mg, 65%). Mp 101–102° C.; $^1$H-NMR (CDCl$_3$): δ 1.40 (m, 2H), 1.65 (m, 4H), 2.02 (m, 2H), 4.13 (sextet, 1H), 5.05 (br, 1H), 6.96 (s, 1H), 7.00 (s, 1H), 7.03 (s, 1H), 8.15 ppm (br, 1H); EI SP/MS: 326 (M+).

Example 18

N-Cyano-N'-(3-methoxy-5-trifluoromethylphenyl)-N"-(3-methylbutyl)guanidine

To a solution of N-Cyano-N'-(3-methoxy-5-trifluoromethyl-phenyl)-O-phenylisourea (0.6 mmol, 200 mg) in dry acetonitrile (1 ml), 3-methylbutylamine (1.31 mmol, 0.152 ml) and triethylamine (0.66 mmol, 0.091 ml) were added. The mixture was stirred for 19 h at 75° C. under nitrogen. After concentration the residue was dissolved in dichloromethane, washed with 1 N aqueous HCl (2×), water, dried (Na$_2$SO$_4$) and concentrated. Crystallisation from ethyl acetate/heptane 1:3 gave white crystals (160 mg, 81%). Mp 105.5–108.5° C.; $^1$H-NMR (CDCl$_3$): δ 0.90 (d, 6H), 1.42 (q, 2H), 1.6 (m,1H), 3.32 (q, 2H), 3.85 (s, 3H), 4.9 (br,1H), 6.94 (brs, 1H), 7.04 (s, 2H), 7.33 ppm (br s, 1H); MA calc for C$_{15}$H$_{19}$F$_3$N$_4$O: C, 54.87%; H, 5.83%; N, 17.06%. Found: C, 55.08%; H, 5.97%; N, 16.68%.

What is claimed is:

1. A compound of formula I

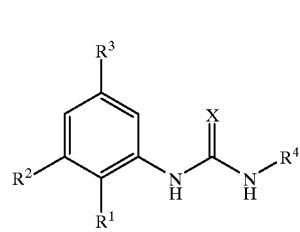

(I)

wherein

R$^1$ and R$^2$ are independently hydrogen, trifluoromethyl or halogen;

R$^3$ is trifluoromethyl, methoxy or halogen;

R$^4$ is straight or branched C$_{1-12}$-alkyl substituted with C$_{3-8}$-cycloalkyl, halogen, hydroxy, aryloxy, arylalkoxy, C$_{1-6}$-alkoxy, C$_{1-6}$-alkylthio, arylthio, C$_{1-6}$-alkylamino, C$_{1-6}$-dialkylamino, heteroaryl, heteroarylalkyl or aryl, wherein the heteroaryl is optionally substituted with halogen or trifluoromethyl; or R$^4$ is C$_{2-12}$-alkenyl, C$_{2-12}$-alkynyl or C$_{3-8}$-cycloalkyl optionally substituted with C$_{3-8}$-cycloalkyl, halogen, hydroxy, aryloxy, arylalkoxy, C$_{1-6}$-alkoxy, C$_{1-6}$-alkylthio, arylthio, C$_{1-6}$-alkylamino, C$_{1-6}$-dialkylamino, heteroaryl, heteroarylalkyl or aryl, wherein the heteroaryl is optionally substituted with halogen or trifluoromethyl; or R$^4$ is Y—R$^5$, wherein Y is —O—or —N(R$^6$)—;

R$^5$ and R$^6$ are independently straight or branched C$_{1-12}$-alkyl, C$_{2-12}$-alkenyl, C$_{2-12}$-alkynyl or C$_{3-8}$-cycloalkyl optionally substituted with C$_{3-8}$-cycloalkyl, halogen, hydroxy, heteroaryl, heteroarylalkyl, aryloxy or aryl, wherein the aryl or heteroaryl is optionally substituted with halogen or trifluoromethyl; or R$^5$ and R$^6$ together with the nitrogen atom form a 3–12 membered mono- or bicyclic system, in which one or more of the carbon atoms may be substituted with nitrogen, oxygen or sulfur, wherein each of these ring systems is optionally mono- or polysubstituted with halogen. C$_{1-6}$-alkyl, hydroxy, C$_{1-6}$-alkoxy, C$_{1-6}$-alkoxy-C$_{1-6}$-alkyl, nitro, amino, cyano, trifluoromethyl, C$_{1-6}$-monoalkyl- or dialkylamino or oxo;

X is N—CN;

or a pharmaceutically acceptable salt thereof, or an optical isomer or mixture of optical isomers thereof, or a tautomeric form thereof.

2. A compound of claim 1, wherein R$^1$ is hydrogen, R$^2$ is hydrogen or trifluoromethyl and R$^3$ is trifluoromethyl.

3. A compound of claim 2, wherein R$^2$ is hydrogen.

4. A compound of claim 2, wherein R$^2$ is trifluoromethyl.

5. A compound of claim 1, wherein R$^1$ is hydrogen and R$^2$ and R$^3$ are chloro.

6. A compound of claim 1, wherein R$^4$ is straight or branched C$_{1-12}$-alkyl substituted with C$_{3-8}$-cycloalkyl, halogen, hydroxy, aryloxy, arylalkoxy, C$_{1-6}$-alkoxy, C$_{1-6}$-alkylthio, arylthio, C$_{1-6}$-alkylamino, C$_{1-6}$-dialkylamino, heteroaryl, heteroarylalkyl or aryl, wherein the heteroaryl is optionally substituted with halogen or trifluoromethyl; or R$^4$ is $C_{2-12}$-alkenyl, $C_{2-12}$-alkynyl or $C_{3-8}$-cycloalkyl optionally substituted with $C_{3-8}$-cycloalkyl, halogen, hydroxy, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl, heteroarylalkyl or aryl, wherein the heteroaryl is optionally substituted with halogen or trifluoromethyl.

7. A compound of claim 6, wherein the heteroarylalkyl is (2-furyl)methyl, (3-furyl)methyl, (2-thienyl)methyl, (3-thienyl)methyl, (2-pyridyl)methyl or 1-methyl-1-(2-pyrimidyl)ethyl.

8. A compound of claim 6, wherein the heteroaryl is 4-pyridinyl.

9. A compound of claim 6, wherein $R^4$ is straight or branched $C_{1-12}$-alkyl substituted with $C_{3-8}$-cycloalkyl, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl, heteroarylalkyl or aryl, wherein the heteroaryl is optionally substituted with halogen or trifluoromethyl.

10. A compound of claim 9, wherein $R^4$ is straight or branched $C_{1-12}$-alkyl substituted with $C_{3-8}$-cycloalkyl, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl or aryl.

11. A compound of claim 10, wherein $R^4$ is straight or branched $C_{1-12}$-alkyl substituted with $C_{3-8}$-cycloalkyl, heteroaryl or aryl.

12. A compound of claim 11, wherein $R^4$ is straight or branched $C_{1-12}$-alkyl substituted with $C_{3-8}$-cycloalkyl.

13. A compound of claim 11, wherein $R^4$ is straight or branched $C_{1-12}$-alkyl substituted with aryl or heteroaryl.

14. A compound of claim 6, wherein $R^4$ is straight or branched $C_{1-12}$-alkyl substituted with halogen, hydroxy, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl or aryl.

15. A compound of claim 14, wherein $R^4$ is straight or branched $C_{1-12}$-alkyl substituted with aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl or aryl.

16. A compound of claim 6, wherein $R^4$ is $C_{3-8}$-cycloalkyl optionally substituted with $C_{3-8}$-cycloalkyl, halogen, hydroxy, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl, heteroarylalkyl or aryl, wherein the heteroaryl is optionally substituted with halogen or trifluoromethyl.

17. A compound of claim 16, wherein $R^4$ is $C_{3-8}$-cycloalkyl substituted with $C_{3-8}$-cycloalkyl, halogen, hydroxy, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl, heteroarylalkyl or aryl, wherein the heteroaryl is optionally substituted with halogen or trifluoromethyl.

18. A compound of claim 19, wherein $R^4$ is $C_{3-8}$-cycloalkyl substituted with $C_{3-8}$-cycloalkyl, aryloxy, arylalkoxy, $C_{1-6}$-alkoxy, $C_{1-6}$-alkylthio, arylthio, $C_{1-6}$-alkylamino, $C_{1-6}$-dialkylamino, heteroaryl, or aryl, wherein the heteroaryl is optionally substituted with halogen or trifluoromethyl.

19. A compound of claim 17, wherein $R^4$ is $C_{3-8}$-cycloalkyl or straight or branched $C_{1-12}$-alkyl substituted with $C_{3-8}$-cycloalkyl.

20. A compound of claim 19, wherein $R^4$ is cyclopentyl, 3-cyclopentylpropyl or 2-cyclopropylethyl.

21. A compound of claim 6, wherein $R^5$ and $R^6$ are independently straight or branched $C_{1-12}$-alkyl, $C_{2-12}$-alkenyl, $C_{2-12}$-alkynyl or $C_{3-8}$-cycloalkyl optionally substituted with $C_{3-8}$-cycloalkyl, halogen, hydroxy, heteroaryl, heteroarylalkyl, aryloxy or aryl.

22. A pharmaceutical composition comprising a therapeutically effective amount of a compound of claim 1 together with one or more pharmaceutically acceptable carriers or diluents.

23. The pharmaceutical composition of claim 22 in the form of an oral dosage unit or parenteral dosage unit.

24. The pharmaceutical composition of claim 23 wherein the compound is administered as a dose in a range from about 0.05 to 1000 mg per day.

25. A method of treating or preventing diseases of the endocrinologic system comprising administering to a subject in need thereof a therapeutically effective amount of a compound of claim 1.

26. A compound which is:
N-Cyano-N'-(3,5-bis(trifluoromethyl)phenyl)-N"-(3-methylbutyl)guanidine,
N-Cyano-N'-(3,5-bis(trifluoromethyl)phenyl)-N"-(1,2,2-trimethylpropyl)guanidine,
N-Cyano-N'-(3,5-bis(trifluoromethyl)phenyl)-N"-(1,2-dimethylpropyl )guanidine,
N-Cyano-N'-[3,5-bis(trifluoromethyl)phenyl]-N"-propyl-guanidine,
N-Cyano-N'-[3,5-bis(trifluoromethyl)phenyl]-N"-(1,1-dimethylpropyl)guanidine,
N-Cyano-N'-(3,5-bis(trifluoromethyl)phenyl)-N"-(1-methylethyl)-guanidine,
N-Cyano-N'-(3-methoxy-5-trifluoromethylphenyl)-N"-(3-methylbutyl)guanidine;
or a pharmaceutically acceptable salt thereof.

27. A pharmaceutical composition comprising a therapeutically effective amount of a compound of claim 28 together with one or more pharmaceutically acceptable carriers or diluents.

28. The pharmaceutical composition of claim 29 in the form of an oral dosage unit or parenteral dosage unit.

29. The pharmaceutical composition of claim 28 wherein the compound is administered as a dose in a range from about 0.05 to 1000 mg per day.

30. A method of treating or preventing diseases of the endocrinologic system comprising administering to a subject in need thereof a therapeutically effective amount of a compound of claim 26.

31. A compound which is:
N-Cyano-N'-(3,5-bis(trifluoromethyl)phenyl)-N"-(2-chlorobenzyl )guanidine,
N-Cyano-N'-(3,5-bis(trifluoromethyl)phenyl)-N"-(3-chlorobenzyl)guanidine,
N-Cyano-N'-(3,5-dichlorophenyl)-N"-(2-chlorobenzyl )guanidine,
N-Cyano-N'-cyclopentyl-N"-(3,5-dichlorophenyl)guanidine,
N-Cyano-N'-cyclopentyl-N"-(3-methyloxy-5-trifluoromethylphenyl)guanidine,
N-Cyano-N'-(3,5-bis(trifluoromethyl)phenyl)-N"-(2-(4-pyridinyl)ethyl)guanidine;
or a pharmaceutically acceptable salt thereof.

32. A pharmaceutical composition comprising a therapeutically effective amount of a compound of claim 31 together with one or more pharmaceutically acceptable carriers or diluents.

33. The pharmaceutical composition of claim 32 in the form of an oral dosage unit or parenteral dosage unit.

34. The pharmaceutical composition of claim 33 wherein the compound is administered as a dose in a range from about 0.05 to 1000 mg per day.

35. A method of treating or preventing diseases of the endocrinologic system comprising administering to a subject in need thereof a therapeutically effective amount of a compound of claim 31.

36. A compound which is:

N-Cyano-N'-(3,5-dichlorophenyl)-N''-(3-cyclopentylpropyl)guanidine,

N-Cyano-N'-(3,5-dichlorophenyl)-N''-(3-cyclopentyl)guanidine,

N-Cyano-N'-(3,5-dichlorophenyl)-N''-(2-cyclopropylethyl)guanidine,

N-Cyano-N'-(3,5-bis(trifluoromethyl)phenyl)-N''-(3-cyclopentylpropyl)guanidine,

N-Cyano-N'-(3,5-bis(trifluoromethyl)phenyl)-N''-(2-cyclopropylethyl)guanidine,

N-Cyano-N'-(3,5-bis(trifluoromethyl)phenyl)-N''-(cyclopentyl)guanidine,

N-Cyano-N'-(3-trifluoromethylphenyl)-N''-cyclopentylguanidine;

N-Cyano-N'-cyclopentyl-N''-(3-methyloxy-5-trifluoromethylphenyl)guanidine or a pharmaceutically acceptable salt thereof.

37. A pharmaceutical composition comprising a therapeutically effective amount of a compound of claim 36 together with one or more pharmaceutically acceptable carriers or diluents.

38. The pharmaceutical composition of claim 37 in the form of an oral dosage unit or parenteral dosage unit.

39. The pharmaceutical composition of claim 38 wherein the compound is administered as a dose in a range from about 0.05 to 1000 mg per day.

40. A method of treating or preventing diseases of the endocrinologic system comprising administering to a subject in need thereof a therapeutically effective amount of a compound of claim 36.

* * * * *